United States Patent [19]

Nakamura et al.

[11] Patent Number: 5,012,012

[45] Date of Patent: Apr. 30, 1991

[54] ALKOXYLATION CATALYST

[75] Inventors: Hirofumi Nakamura, Narashino; Yuichi Nakamoto, Nagareyama; Yuji Fujimori, Narashino, all of Japan

[73] Assignee: Lion Corporation, Tokyo, Japan

[21] Appl. No.: 342,906

[22] Filed: Apr. 25, 1989

Related U.S. Application Data

[62] Division of Ser. No. 248,954, Sep. 26, 1988, abandoned.

[30] Foreign Application Priority Data

Sep. 29, 1987 [JP] Japan ................. 62-242499

[51] Int. Cl.$^5$ ............................................. C07C 41/03
[52] U.S. Cl. ................................. 568/618; 260/410.6
[58] Field of Search ........................ 568/618; 260/410.6

[56] References Cited

U.S. PATENT DOCUMENTS

| | | | |
|---|---|---|---|
| 4,278,820 | 7/1981 | Kametaka et al. | 568/618 |
| 4,465,877 | 8/1984 | Edwards | 568/618 |
| 4,593,135 | 6/1986 | Gregory | 568/618 |

FOREIGN PATENT DOCUMENTS

| | | | |
|---|---|---|---|
| 1185992 | 4/1985 | Canada | 568/618 |
| 1481895 | 8/1977 | United Kingdom | 568/618 |

*Primary Examiner*—Howard T. Mars
*Attorney, Agent, or Firm*—Bacon & Thomas

[57] ABSTRACT

An alkoxylation catalyst for causing an alkylene oxide to react with an organic compound having one or more active hydrogen, comprising magnesium oxide modified by the addition of at least one metal ion selected from the group consisting of $Al^{3+}$, $Ga^{3+}$, $In^{3+}$, $Tl^{3+}$, $Co^{3+}$, $Sc^{3+}$, $La^{3+}$, and $Mn^{2+}$. In the presence of the catalyst, an addition polymerization reaction between the alkylene oxide and the organic compound having one or more active hydrogen such as an alcohol or phenol can be performed with only small amounts of unreacted material and byproducts, and the alkylene oxide adduct having a very narrow alkylene oxide adduct distribution can be obtained.

18 Claims, 2 Drawing Sheets

ALKOXYLATION CATALYST

This application is a division of application Ser. No. 248,954 filed Sept. 26, 1988, now abandoned.

BACKGROUND OF THE INVENTION

1. Field of the Invention

The present invention relates to an alkoxylation catalyst and, more particularly, to an alkoxylation catalyst containing magnesium oxide as a major constituent.

2. Description of the Prior Art

An alkylene oxide adduct of an organic compound having one or more active hydrogen, such as an alcohol or phenol, is a valuable compound which is used in a variety of applications such as a solvent, a surfactant, and various intermediate chemical products. An alkoxylation reaction for producing such an alkylene oxide adduct is performed in the presence of an acid or alkali catalyst according to the following formula:

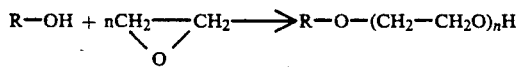

Examples of the conventional catalyst used in the above reaction are: a soluble, strong basic compound of an alkali metal such as lithium, sodium, potassium, rubidium, or cesium; a halide of a metal such as boron, tin, zinc, antimony, iron, nickel, or aluminum; an acid such as sulfuric acid or phosphoric acid; and a phosphate, a sulfate, a perchlorate, an oxalate, a carboxylate, and an acetate of a metal such as magnesium, zinc, or calcium.

These catalysts, however, have the following drawbacks. When the molar number of an alkylene oxide adduct is increased, an acid catalyst such as Lewis acid or a Friedel-Crafts catalyst causes a side reaction to produce a large amount of undesirable byproducts such as dioxane, dioxolane, or polyalkylene glycol. In addition, the acid catalyst has many disadvantages as an industrial catalyst. For example, the acid catalyst strongly corrodes metals. An adduct having a wide alkylene oxide adduct distribution can be obtained by a strong basic catalyst such as caustic potash or caustic soda. When soluble, basic compound catalysts of alkyl earth metals as described in U.S. Pat. Nos. 4,210,764, 4,223,164, 4,239,917, and 4,302,613 are used, the alkylene oxide adduct distribution can be narrower than that obtained with a conventional strong alkali catalyst, but is still wider than that obtained with the acid catalyst.

SUMMARY OF THE INVENTION

It is an object of the present invention to provide an alkoxylation catalyst for producing an alkylene oxide adduct having a narrow alkylene oxide adduct distribution with only small amounts of unreacted material and byproducts.

According to the present invention, there is provided an alkoxylation catalyst comprising magnesium oxide modified by the addition of at least one metal ion selected from the group consisting of $Al^{3+}$, $Ga^{3+}$, $In^{3+}$, $Tl^{3+}$, $Co^{3+}$, $Sc^{3+}$, $La^{3+}$, and $Mn^{2+}$.

According to the alkoxylation catalyst of the present invention, an addition polymerization reaction between the alkylene oxide and an organic compound having one or more active hydrogen such as an alcohol or phenol is performed with small amounts of unreacted material and byproducts. And the alkylene oxide adduct having a narrow alkylene oxide adduct distribution is obtained.

DETAILED DESCRIPTION OF THE PREFERRED EMBODIMENTS

Figure 2:
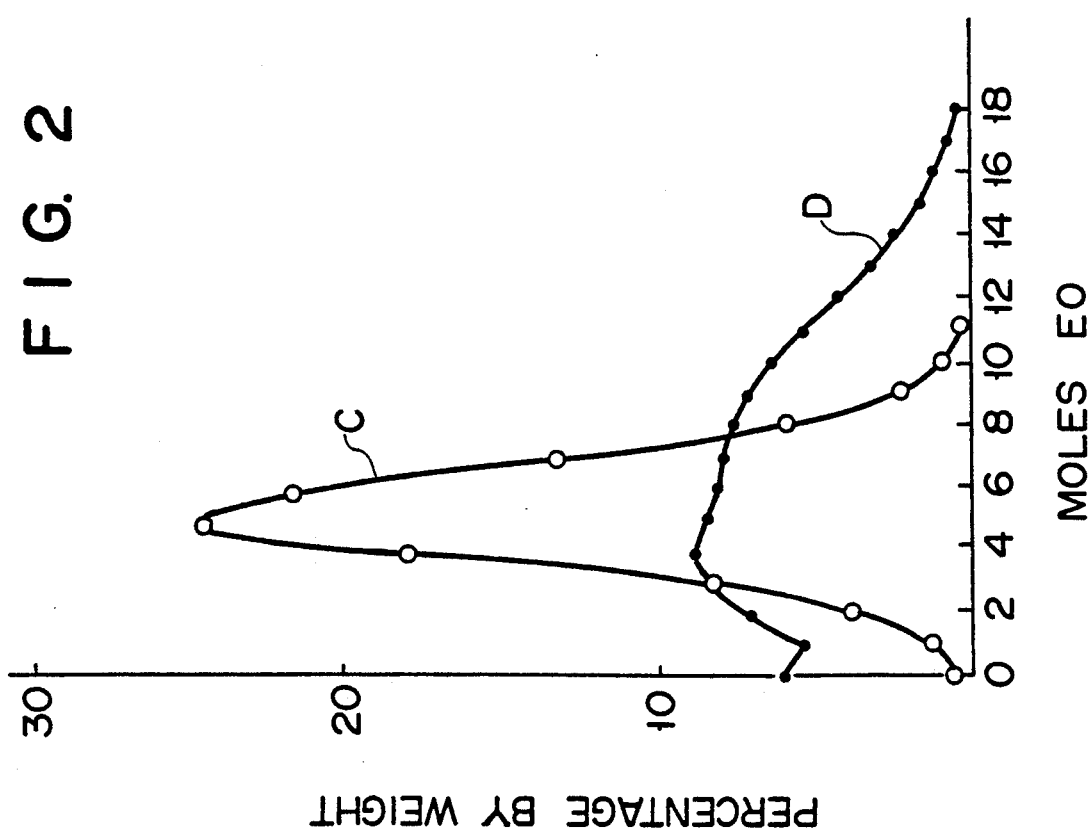
FIG. 2 is a graph comparing an EO adduct distribution of an ethoxylate obtained by using a catalyst according to another embodiment of the present invention and that of an ethoxylate obtained by using a conventional catalyst.

A catalyst according to the present invention is very effective as a catalyst for obtaining an alkylene oxide adduct by an addition polymerization reaction between an alkylene oxide and an organic compound having one or more active hydrogen.

The organic compound having one or more active hydrogen which is used in the present invention may be any compound if it can be alkoxylated. Examples of such an organic compound are alcohols, phenols, polyols, carboxylic acids, thiols, amines, and a mixture consisting of at least two thereof.

Any alkylene oxide may be used in the present invention if it is reacted with an organic compound having one or more active hydrogen to produce an adduct. A preferable example is a vicinal alkylene oxide having 2 to 8 carbon atoms. The most preferable alkylene oxide is an ethylene oxide, a propylene oxide, or a mixture thereof.

A content of $Al^{3+}$, $Ga^{3+}$, $In^{3+}$, $Tl^{3+}$, $Co^{3+}$, $Sc^{3+}$, $La^{3+}$, or $Mn^{2+}$ added to magnesium oxide is preferably 0.1 to 30 wt % of the total content of the catalyst, and more preferably 0.5 to 20 wt %.

A method of manufacturing a catalyst of the present invention is not limited to a specific method. However, a known method is used as a method of preparing a multimetallic oxo compound. For example, magnesium oxide having a purity of 99% or more is impregnated with a nitrate or carbonate aqueous solution containing $Al^{3+}$, $Ga^{3+}$, $In^{3+}$, $Tl^{3+}$, $Co^{3+}$, $Sc^{3+}$, $La^{3+}$, or $Mn^{2+}$. The impregnated magnesium oxide is calcinated in a nitrogen gas flow or in a vacuum at 400° to 1,000° C. and more preferably 500° to 800° C. (impregnation method). Alternatively, magnesium nitrate and nitrates of the above metals are mixed at a predetermined mixing ratio, and the resultant mixture is dissolved in water to prepare an aqueous solution. A hydrate of a hydroxide or a composite oxide is coprecipitated, filtered, washed, and dried. The dried powder is then calcinated in the same manner as in the impregnation method. The second method is called coprecipitation method. Furthermore, a laminar compound (hydrotalcite) represented by general formula $Mg_{1-x}Al_x(OH)_2(CO_3)_{x/2} \cdot m\text{-}H_2O$ or a compound obtained by substituting metal ion $Al^{3+}$ in the formula with $Ga^{3+}$, $In^{3+}$, $Tl^{3+}$, $Co^{3+}$, $Sc^{3+}$, or $La^{3+}$ is calcinated following the same procedures as in the impregnation method, thereby obtaining a composite oxide.

A linear- or branched primary or secondary alcohol having 2 to 30 carbon atoms is preferably used as the organic compound having one or more hydrogen. A primary alcohol having 6 to 24 carbon atoms is more preferably used. These alcohols are not only used singly but also used as a mixture of two or more alcohols. Typical examples of the alcohols are a linear primary alcohol (e.g., n-octanol, n-decanol, n-dodecanol, or n-tetradecanol), a branched secondary alcohol (e.g., 5-ethylnonanol-2, 2,5,8-trimethyl-4,2-methyl-7-ethylundecanol-4, or 3,9-diethyltridecanol-6), a branched primary oxoalcohol having 8 to 22 carbon atoms, DOBADOL-23 (tradename; a mixture of C12/C13=45/55; about 80% linear, about 20% branched) available from Mitsubishi Petrochemical Co., Ltd., DIADOL-13 (tradename; C13; straight-chain ratio: about 50%) available from Mitsubishi Chemical Industries Ltd., and NEODOL-23 (tradename; mixture of C12/C13=45/55; about 80% linear) available from Shell Chemical Co.

The alkoxylation reaction using the catalyst of the present invention can be easily performed in accordance with conventional procedures and reaction conditions. A reaction temperature is preferably 80° to 230° C., more preferably 120° to 180° C., and most preferably 120° to 160° C. When the reaction temperature is excessively low, the reaction rate is too low. However, when the reaction temperature is excessively high, a product is undesirably decomposed. A reaction pressure is preferably 0 to 20 atm and more particularly 2 to 8 atm although it depends on the reaction temperature.

Although the content of the catalyst varies depending on a molar ratio of the alkylene oxide and alcohol or the like used in the reaction, the content preferably falls within the range of 0.1 to 20 wt % of the content of the alcohol or the like, and more preferably 0.5 to 6 wt %.

The alkoxylation reaction using the catalyst of the present invention can be performed as follows. For example, an alcohol and a catalyst are charged in an autoclave. An alkylene oxide is supplied to the autoclave to cause it to react with the alcohol in a nitrogen atmosphere in the presence of the catalyst under the predetermined temperature and pressure conditions. The product is cooled, and the catalyst is filtered.

The product obtained by using the catalyst of the present invention is essentially neutral. Unlike the conventional method, the product need not be neutralized by adding an acid or alkali. The present invention will be described in detail by way of its examples and comparative examples.

Example 1

20 g of a magnesium oxide powder (MgO, purity of 99%) were dissolved in 500 g of a 1% aluminum nitrate aqueous solution, and the resultant solution was sufficiently stirred and dried to obtain a solid product. The solid product was dried overnight at 110° C. and was pulverized. The pulverized product was gradually heated in a nitrogen gas flow and calcinated at 600° C. for 2 hours to obtain a catalyst. The content of $Al^{3+}$ in the catalyst was 3 wt %.

120 g of lauryl alcohol having a water content of 100 ppm and 2.5 g of the catalyst were charged in an autoclave, and the air in the autoclave was substituted by nitrogen gas. The autoclave content was heated while being stirred. The temperature was maintained at 160° C., and the pressure was maintained at 3 atm. 84 g of an ethylene oxide (EO) were introduced into the autoclave and were reacted with lauryl alcohol in the presence of the catalyst for about 2 hours. The reacted solution was cooled to 70° C., and the catalyst was filtered.

Figure 1:
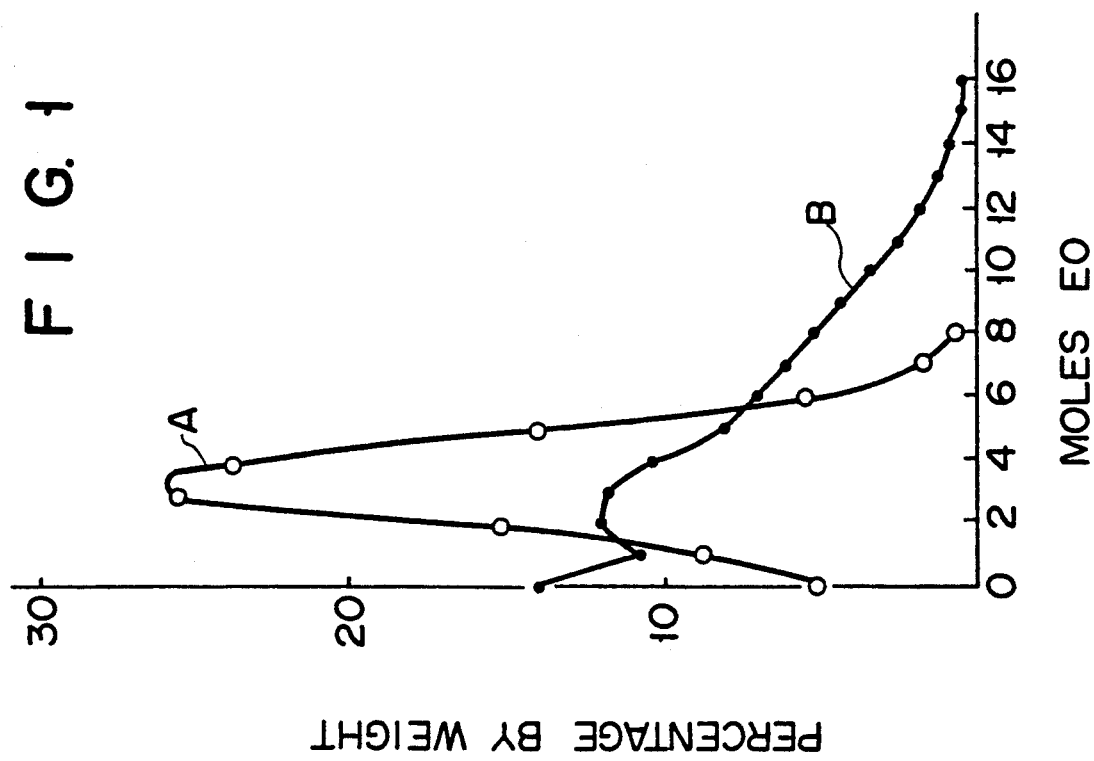
FIG. 1 is a graph comparing an EO (ethylene oxide) adduct distribution of an ethoxylate obtained by using a catalyst according to an embodiment of the present invention and that of an ethoxylate obtained by using a conventional catalyst.

An average EO adduct molar number of the resultant ethoxylate was measured by to be 3.0. The EO adduct molar distribution of the ethoxylate was plotted as indicated by curve A in FIG. 1. As shown in FIG. 1, the wt % of each ethoxylate component with respect to the ethoxylate weight is plotted along the ordinate, and the EO adduct molar number is plotted along the abscissa. Curve B represents an EO adduct molar distribution of an ethoxylate obtained by using a conventional NaOH catalyst, as shown in Comparative Example 2 (to be described later).

As is apparent from a comparison between curves A and B, the ethoxylate obtained by using the catalyst of the present invention has a very narrow EO adduct molar distribution as compared with the ethoxylate obtained by the conventional catalyst.

The content of the unreacted alcohol was as very small as 5.2 wt %, and the content of polyethylene glycol as a byproduct was as very small as 0.1 wt %.

Example 2

A reaction was performed following the same procedures as in Example 1 except that the content of the catalyst was 5 g, and the reaction temperature was 180° C.

Following the same procedures as in Example 1, the average EO adduct molar number of the resultant ethoxylate, the content of the unreacted alcohol, and the content of polyethylene glycol as a byproduct were measured to be 5.7, 0.1 wt %, and 1 wt %, respectively. The EO adduct molar distribution of the ethoxylate obtained by using the catalyst of the present invention is very narrow as compared with the ethoxylate obtained by using the conventional catalyst, as shown in FIG. 2. Referring to FIG. 2, curve C represents the EO adduct molar distribution of the ethoxylate obtained in Example 1, while curve D represents an EO adduct molar distribution of an ethoxylate prepared by using a conventional NaOH in Comparative Example 2 (to be described later).

Example 3

A $Ga^{3+}$ ion-contained MgO catalyst was prepared following the same procedures as in Example 1 except that 500 g of a 0.9% gallium nitrate aqueous solution were used in place of 500 g of a 1% aluminum nitrate aqueous solution. The content of $Ga^{3+}$ in this catalyst was 6 wt %.

A reaction was performed following the same procedures as in Example 1 except that 5 g of the catalyst and 93 g of EO were used and the reaction time was 1.5 hours.

Figure 3:
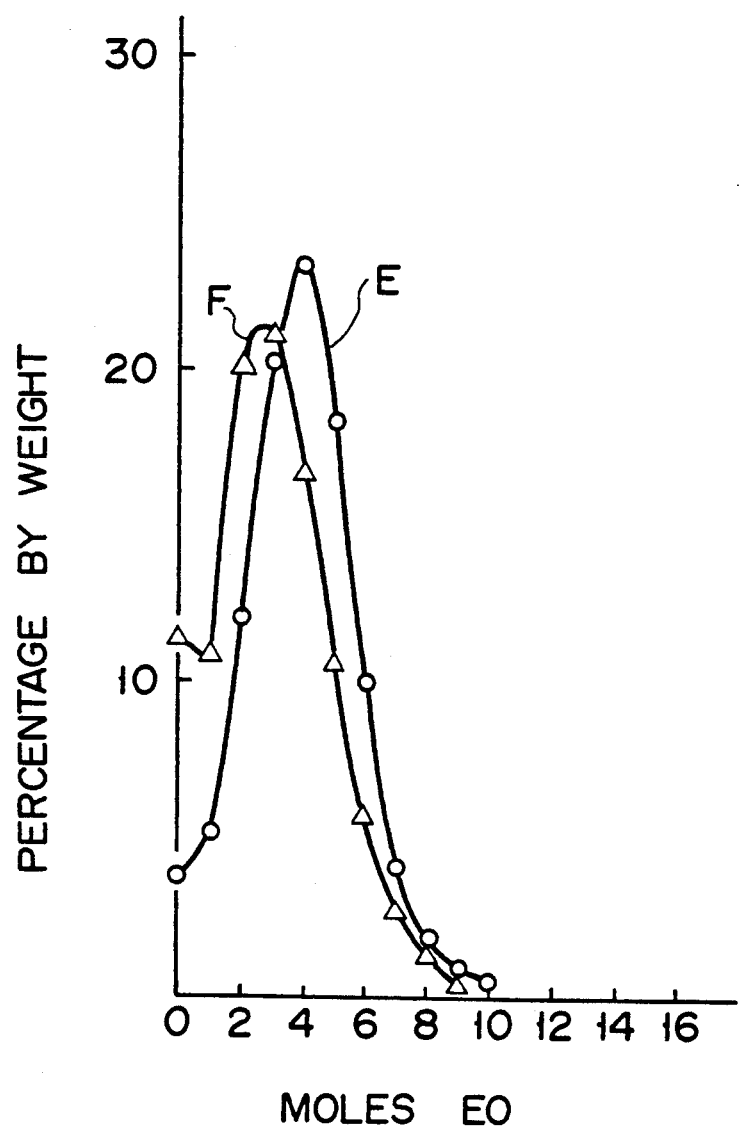
FIG. 3 is a graph showing an EO adduct distribution of an ethoxylate using a catalyst according to still another embodiment of the present invention.

Following the same procedures as in Example 1, the average EO adduct molar number of the ethoxylate of the product, and the content of the unreacted alcohol were measured to be 3.3 and 3.8 wt %, respectively. The EO adduct molar distribution of the ethoxylate is apparently very narrow, as indicated by curve E in FIG. 3.

Example 4

A $Mn^{2+}$ ion-contained MgO catalyst was obtained following the same procedures as in Example 1 except that 500 g of a 0.5% manganese nitrate aqueous solution were used in place of 500 g of a 1% aluminum nitrate aqueous solution. The content of $Mn^{2+}$ in the catalyst was 3 wt %.

A reaction was performed following the same procedures as in Example 1 except that 5 g of the catalyst and 67 g of EO were used and the reaction time was 6 hours.

Following the same procedures as in Example 1, the average EO adduct molar number of the resultant ethoxylate, and the content of the unreacted alcohol were measured to be 2.4 and 11.3 wt %, respectively. The EO adduct molar distribution of the ethoxylate is apparently very narrow, as indicated by curve F in FIG. 3.

Comparative Example 1

Only 20 g of an MgO powder (purity of 99%) were heated in a nitrogen gas flow to prepare a catalyst following the same procedures as in Example 1. A reaction was performed as in Example 1. However, the catalyst did not function as a catalyst at all.

Comparative Example 2

376 g of lauryl alcohol and 0.2 g of caustic soda (0.05 wt %/lauryl alcohol) were charged in an autoclave, and the air in the autoclave was substituted by nitrogen gas. The mixture in the autoclave was dehydrated while being heated to 130° C. at a reduced pressure and being stirred. The temperature was increased to 180° C., and the pressure was maintained at 3 atm. 260 g of an EO were introduced into the autoclave and were reacted with lauryl alcohol for about 2 hours.

An average EO adduct molar number of the resultant ethoxylate was 2.9. The content of the unreacted alcohol was as very large as 14 wt %, and the content of polyethylene glycol as a byproduct was as very large as 1 wt %. The EO adduct molar distribution of the ethoxylate was plotted as indicated by curve B in FIG. 1.

As is apparent from a comparison between curves A and B, the ethoxylate obtained by using the conventional catalyst has a very wide EO adduct molar distribution as compared with the ethoxylate obtained by using the catalyst of the present invention.

Comparative Example 3

A reaction was performed following the same procedures as in Comparative Example 2 except that 440 g of EO were used and the reaction time was 6 hours.

Following the same procedures as in Example 1, the average EO adduct molar number of the ethoxylate of the product, and the content of the unreacted alcohol were measured to be 5.0 and 6 wt %, respectively. The EO adduct molar distribution of the ethoxylate is apparently very wide, as indicated by curve D in FIG. 2, as compared with the ethoxylate (curve C) obtained by using the catalyst of the present invention.

Example 5

140 g of 9-hydroxymethyl methylstearate and 5.5 g of the catalyst in Example 1 were charged in an autoclave, and the air in the autoclave was substituted by nitrogen gas. After the internal pressure of the autoclave was reduced to 1 mmHg or less, the charged content was dehydrated while being heated to 130° C. for one hour under stirring. The product was heated to 120° C. While the pressure was maintained at 3 to 5 atm, 95 g of an EO were introduced into the autoclave and were reacted with 9-hydroxymethyl methylstearate in the presence of the catalyst for about 6.0 hours. The average EO adduct molar number of the resultant ethoxylate was 5.0.

Example 6

318 g of magnesium nitrate (hexahydrate) and 21.5 g of aluminum nitrate (nonahydrate) were dissolved in 1,250 g of pure water to obtain an aqueous solution, and 250 ml of a 28% ammonia water were added to the aqueous solution to perform coprecipitation. A precipitate was filtered and washed with water, and then was dried at 110° C. The dried precipitate was sifted with a mesh of 20 to 50. The resultant powder was gradually heated in a nitrogen gas flow and heated at 600° C. for 2 hours, thereby obtaining a catalyst.

An ethoxylation reaction was performed following the same procedures as in Example 1 except that the resultant catalyst was used and the reaction temperature was 140° C. The average EO adduct molar number of the resultant ethoxylate was 3.0. The content of the unreacted alcohol and the EO adduct molar distribution were similar to those in Example 1.

Example 7

An ethoxylation reaction was performed following the same procedures as in Example 1 except that 7.4 g of the catalyst in Example 6, 369 g of lauryl alcohol, and 1,039 g of the EO were used, and the reaction time was about 3.5 hours. The average EO adduct molar number of the resultant ethoxylate was 11.9.

Example 8

512 g of DOBANOL-23 (Mitsubishi Petrochemical Co., 25 Ltd.) and 10 g of the catalyst in Example 6 were charged in an autoclave, and 349 g of the EO were added thereto following the same procedures and conditions as in Example 6 to perform an ethoxylation reaction for about 2 hours. The average EO adduct molar number of the resultant ethoxylate was 3.0.

Example 9

496 g of DOBANOL-13 (Mitsubishi Petrochemical Co., Ltd.) and 20 g of the catalyst in Example 6 were charged in an autoclave, and 1,941 g of the EO were added thereto following the same procedures and conditions as in Example 6 to perform an ethoxylation reaction for about 5.5 hours. The average EO adduct molar number of the resultant ethoxylate was 17.2.

Example 10

318 g of magnesium nitrate (hexahydrate) and 21.5 g of aluminum nitrate (nonahydrate) were dissolved in 500 g of distilled water to obtain an aqueous solution, and 500 ml of a 28% ammonia water were added to the aqueous solution to perform coprecipitation. A precipitate was filtered and washed with water, and then was dried at 110° C. The dried precipitate was sifted with a screen of 20-150 mesh. The resultant powder was gradually heated in a nitrogen gas flow and calcinated at 600° C. for 2 hours, thereby obtaining a catalyst.

An ethoxylation reaction was performed following the same procedures as in Example 1 except that 1.5 g of the resultant catalyst were used and the reaction temperature was 140° C. The average EO adduct molar number of the resultant ethoxylate was 3.0. The content of the unreacted alcohol and the EO adduct molar distribution were similar to those in Example 1.

Example 11

100 g of hydrotalcite having a chemical composition of $Mg_6Al_2(OH)_{16}(CO_3)\cdot 4H_2O$ were gradually heated to 600° C. at a pressure of 0.1 Torr and calcinated at 600° C. for 2 hours to obtain 55 g of a catalyst powder.

An ethoxylation reaction was performed following the same procedures as in Example 1 except that 1.5 g of the resultant catalyst were used and the reaction temperature was 180° C. The average EO adduct molar number of the resultant ethoxylate was 3.0. The content of the unreacted alcohol and the EO adduct moar distribution were similar to those in Example 1.

What is claimed is:

1. A method of producing an alkylene oxide adduct of an organic compound having one or more active hydrogen which comprises reacting an organic compound having one or more active hydrogen with an alkylene oxide in the presence of an alkoxylation catalyst consisting essentially of magnesium oxide modified by the addition of at least one metal ion selected from the group consisting of $Al^{3+}$, $Ga^{3+}$, $In^{3+}$, $Tl^{3+}$, $Co^{3+}$, $Sc^{3+}$, $La^{3+}$, or $Mn^{2+}$.

2. The method according to claim 1, wherein the metal ion is $Al^{3+}$ or $Ga^{3+}$.

3. A method according to claim 1, wherein a content of the metal ion is 0.1 to 30 wt %.

4. A method according to claim 1, wherein a content of the metal ion is 0.5 to 20 wt %.

5. A method according to cliam 1, wherien the number of carbon atoms of the alkylene oxide is 2 to 8.

6. A method according to claim 1, wherein the organic compound having one or more active hydrogens is at least one alkanal reactant.

7. A method according to claim 1 wherein said alkanal reactant are linear or branched primary or secondary alkanals each having 2 to 30 carbon atoms.

8. A method according to claim 1, wherein said alkanal reactant are primary alkanals each having 6 to 24 carbon atoms.

9. A method according to claim 6, wherein the alkanal reactant is at least one selected from the group consisting of n-octanol; n-decanol; n-dodecanol; n-tetradecanol; n-octadeconal; 5-ethylnonanol-2; 2,5,8-trimethylnonanol-4; 2-methyl-7-ethylundecanol-4; 3,9-diethyltridecanol-6; and a branched primary oxoalcohol having 8 to 22 carbon atoms.

10. A method according to claim 1, wherein the alkylene oxide is the vicinal alkylene oxide having 2 to 8 carbon atoms.

11. A method according to claim 1, wherein the alkylene oxide is ethylene oxide, propylene oxide, or a mixture thereof.

12. A method according to claim 1, wherein a reaction temperature falls within the range of 80° to 230° C.

13. A method according to claim 1, wherein a reaction temperature falls within the range of 120° to 180° C.

14. A method according to claim 1, wherein a reaction temperature falls within the range of 120° to 180° C.

15. A method according to cliam 1, wherien areaction pressure falls within the range of 0 to 20 atm.

16. A method according to claim 1, wherein a reaction pressure falls within the range of 2 to 8 atm.

17. A method according to claim 1, wherien an amount of the catalyst falls within the range of 0.1 to 20% based on teh weight of the organic compound.

18. A method according to claim 1, wherein an amount of the catalyst falls within the range of 0.5 to 6% based on the weight of the organic compound.

* * * * *